US007048945B2

(12) United States Patent
Percel et al.

(10) Patent No.: US 7,048,945 B2
(45) Date of Patent: May 23, 2006

(54) TIMED PULSATILE DRUG DELIVERY SYSTEMS

(75) Inventors: Phillip J. Percel, Troy, OH (US); Krishna S. Vishnupad, Dayton, OH (US); Gopi M. Venkatesh, Vandalia, OH (US); Der Yang Lee, Flemington, NJ (US)

(73) Assignee: Eurand Pharmaceuticals, Ltd. (IE)

( * ) Notice: Subject to any disclaimer, the term of this patent is extended or adjusted under 35 U.S.C. 154(b) by 273 days.

(21) Appl. No.: 10/675,656

(22) Filed: Sep. 30, 2003

(65) Prior Publication Data

US 2005/0118268 A1  Jun. 2, 2005

Related U.S. Application Data

(62) Division of application No. 09/778,645, filed on Feb. 7, 2001, now Pat. No. 6,627,223.

(60) Provisional application No. 60/181,867, filed on Feb. 11, 2000.

(51) Int. Cl.
*A61K 9/26* (2006.01)
*A61K 9/40* (2006.01)

(52) U.S. Cl. ............ 424/471; 424/464; 424/468; 424/469; 424/458; 424/457; 424/490; 424/492

(58) Field of Classification Search ............ 424/471, 424/468, 469, 490, 492, 464
See application file for complete search history.

(56) References Cited

U.S. PATENT DOCUMENTS

| | | | |
|---|---|---|---|
| 3,184,386 A | 5/1965 | Stephenson | |
| 3,558,768 A | 1/1971 | Klippel | |
| 4,369,172 A | 1/1983 | Schor et al. | |
| 4,389,393 A | 6/1983 | Schor et al. | |
| 4,713,248 A | 12/1987 | Kjornaes et al. | |
| 4,716,041 A | 12/1987 | Kjornaes et al. | |
| 4,752,470 A | 6/1988 | Mehta | |
| 4,840,799 A | 6/1989 | Appelgren et al. | |
| 4,851,229 A | 7/1989 | Magruder et al. | |
| 4,871,549 A | 10/1989 | Ueda et al. | |
| 4,892,741 A | 1/1990 | Ohm et al. | |
| 5,011,692 A | 4/1991 | Fujioka et al. | |
| 5,017,381 A | 5/1991 | Maruyama et al. | |
| 5,026,559 A * | 6/1991 | Eichel et al. | 424/458 |
| 5,133,974 A | 7/1992 | Paradissis et al. | |
| 5,229,135 A | 7/1993 | Philippon et al. | |
| 5,260,068 A | 11/1993 | Chen | |
| 5,260,069 A | 11/1993 | Chen | |
| 5,472,708 A | 12/1995 | Chen | |
| 5,508,040 A | 4/1996 | Chen | |
| 5,536,507 A | 7/1996 | Abramowitz et al. | |
| 5,567,441 A | 10/1996 | Chen | |
| 5,837,284 A | 11/1998 | Mehta et al. | |
| 5,837,379 A | 11/1998 | Chen et al. | |
| 5,840,329 A | 11/1998 | Bai | |
| 5,900,252 A | 5/1999 | Calanchi et al. | |
| 6,024,982 A | 2/2000 | Oshlack et al. | |
| 6,096,340 A | 8/2000 | Chen et al. | |
| 6,099,859 A | 8/2000 | Cheng et al. | |
| 6,099,863 A | 8/2000 | Gilis et al. | |
| 6,103,263 A | 8/2000 | Lee et al. | |
| 6,106,862 A | 8/2000 | Chen et al. | |
| 6,627,223 B1 * | 9/2003 | Percel et al. | 424/471 |

FOREIGN PATENT DOCUMENTS

EP  0391518  10/1990

OTHER PUBLICATIONS

International Search Report issued Jun. 19, 2001 in corresponding PCT Int'l. Appln. PCT/US01/04012.
Ishino, R. et al., "Design and Preparation of Pulsatile Release Tablet as a New Oral Drug Delivery System," *Chem. Pharm. Bull.*, vol. 40, No. 11, pp. 3036-3041 (Nov. 1992).

* cited by examiner

*Primary Examiner*—Thurman K. Page
*Assistant Examiner*—Lakshmi Channavajjala
(74) *Attorney, Agent, or Firm*—Thompson Hine LLP

(57) ABSTRACT

A pharmaceutical dosage form such as a capsule capable of delivering therapeutic agents into the body in a time-controlled or position-controlled pulsatile release fashion, is composed of a multitude of multicoated particulates (beads, pellets, granules, etc.) made of one or more populations of beads. Each of these beads except an immediate release bead has at least two coated membrane barriers. One of the membrane barriers is composed of an enteric polymer while the second membrane barrier is composed of a mixture of water insoluble polymer and an enteric polymer. The composition and the thickness of the polymeric membrane barriers determine the lag time and duration of drug release from each of the bead populations. Optionally, an organic acid containing intermediate membrane may be applied for further modifying the lag time and/or the duration of drug release. The pulsatile delivery may comprise one or more pulses to provide a plasma concentration-time profile for a therapeutic agent, predicted based on both its pharmaco-kinetic and pharmaco-dynamic considerations and in vitro/in vivo correlations.

20 Claims, No Drawings

TIMED PULSATILE DRUG DELIVERY SYSTEMS

CROSS REFERENCE TO RELATED APPLICATIONS

This application is a divisional of application Ser. No. 09/778,645, filed Feb. 7, 2001, now U.S. Pat. No. 6,627,223, which claims priority from U.S. Provisional Application No. 60/181,867 filed Feb. 11, 2000.

BACKGROUND OF THE INVENTION

Oral dosage forms are known which provide a zero order or first order release in which the drug is released at a substantially steady rate of release per unit of time. These dosage forms are satisfactory for the administration of pharmaceutical dosage forms of many drugs. However, there are instances where maintaining a constant blood level of a drug is not desirable. In such cases (e.g., optimization of chemotherapy, reducing nocturnal or early morning systems of chronic diseases such as ischemic heart disease, asthma, arthritis, avoiding developing a tolerance to nitrates, antibiotics and steroidal contraceptives, or where absorption windows exist), a 'time-controlled' pulsatile drug delivery system may be more advantageous. There are also instances in which a 'position-controlled' drug delivery system (e.g. treatment of colon disease or use of colon as an absorption site for peptide and protein based products) may prove to be more efficacious.

A pulsatile delivery system is capable of providing one or more immediate release pulses at predetermined time points after a controlled lag time or at specific sites. However, there are only a few such orally applicable pulsatile release systems due to the potential limitation of the size or materials used for dosage forms. Ishino et al. disclose a dry-coated tablet form in Chemical Pharm. Bull. Vol. 40 (11), p3036–3041 (1992). U.S. Pat. No. 4,851,229 issued Jul. 25, 1989 to P. R. Magruder et al., U.S. Pat. No. 5,011,692 issued Apr. 30, 1991 to K. Fujioka et al., U.S. Pat. No. 5,017,381 issued May 21, 1991 to Maruyama and R. Cortese, U.S. Pat. No. 5,229,135 issued Jul. 20, 1993 to F. Philippon et al., and U.S. Pat. No. 5,840,329 issued Nov. 24, 1998 to J. P.-F. Bai disclose preparation of pulsatile release systems. Some other devices are disclosed in U.S. Pat. Nos. 4,871,549 issued Oct. 3, 1989 to Y. Ueda et al., U.S. Pat. No. 5,260,068 and U.S. Pat. No. 5,260,069 both issued Nov. 9, 1993 to C. M. Chen and U.S. Pat. No. 5,508,040 issued Apr. 16, 1996 to C. M. Chen. U.S. Pat. No. 5,229,135 issued Jul. 20, 1993 and U.S. Pat. No. 5,567,441 issued Oct. 22, 1996 both to C. M. Chen disclose a pulsatile release system consisting of pellets coated with delayed release or water insoluble polymeric membranes incorporating hydrophobic water insoluble agents or enteric polymers to alter membrane permeability. U.S. Pat. No. 5,837,284 issued Nov. 17, 1998 to A. M. Mehta et al. discloses a dosage form which provides an immediate release dose of methylphenidate upon oral administration, followed by one or more additional doses spread over several hours. Thus there is a need for a pulsatile drug delivery system which is intended to provide for the simultaneous delivery of a single or a combination of drug substances as well as time-controlled series of pulses for efficacious treatment of diseases with maximum patient compliance and minimum side effects. Provision of a single targeted pulse several hours after oral administration, with or without an immediate release pulse upon oral administration, is a desired manifestation of the timed pulsatile release drug delivery systems of the present invention.

SUMMARY OF THE INVENTION

The present invention provides a method for manufacturing a pharmaceutically elegant multi-particulate dosage form having timed pulsatile release characteristics, i.e., a well time-controlled series of pulses occurring several hours after oral administration, with or without an immediate release pulse upon oral administration. The present invention also provides a novel multicoated particulate dosage form having an active core and a first membrane of an enteric polymer and a second membrane of a mixture of water insoluble and enteric polymers. An organic acid containing membrane may be provided between the first and second membrane layers referred to above to provide for time-separated pulses. While the membranes can be applied in any order, the enteric polymer membrane is usually applied as the innermost membrane.

DETAILED DESCRIPTION OF THE INVENTION

The active core of the novel dosage form of the present invention may be comprised of an inert particle such as a commercially available non-pareil sugar sphere. The amount of drug in the core will depend on the drug and the dose that is desired. Generally, the core will contain about 5 to 60% by weight of the drug based on the total weight of the core. Those skilled in the art will be able to select an appropriate amount of drug for coating or incorporation into the core to achieve the desired dosage form.

An aqueous or a pharmaceutically acceptable solvent medium may be used for preparing core particles. The type of inert binder that is used to bind the water soluble drug to the inert particle is not critical but usually water soluble or alcohol soluble binders are used. Binders such as polyvinylpyrrolidone (PVP), carboxyalkylcelluloses, polyethylene oxide, polysaccharides such as dextran, corn starch, hydroxypropyl methylcellulose (HPMC), hydroxypropylcellulose, may be used by dispersing them in water at a concentration of from about 0.5 to 5 weight %. The drug substance may be present in this coating formulation in the solution form or may be suspended. The drug concentration may vary from about 10 to 30 weight % depending on the viscosity of the coating formulation.

In one embodiment, the active core may be prepared by granulation or by extrusion and spheronization. The drug substance, a binder such as PVP, an optional dissolution rate controlling polymer such as high viscosity HPMC, and optionally other pharmaceutically acceptable excipients are blended together in a high shear granulator, such as Fielder granulator, or a a fluid bed granulator, such as Glatt GPCG granulator, and granulated to form agglomerates by adding/spraying a granulating fluid such as water or alcohol and dried. The wet mass can be extruded and spheronized to produce spherical particles (beads) using an extruder/marumerizer. In these embodiments, the drug load could be as high as 90% by weight based on the total weight of the extruded or granulated core.

One of the layers of membrane coating on the water soluble/dispersible drug containing particle may comprise a plasticized enteric polymer while the other layer may comprise a mixture of a water insoluble polymer and a plasticized water dispersible/enteric polymer wherein said water insoluble polymer and said water dispersible polymer may be present at a weight ratio of 10:1 to 1:1 and typically about 4:1 to 1:1 and the total weight of the coatings is about 15 to 80 weight % and more typically about 20 to 60 weight % based on the total weight of the multiparticulate dosage form.

The intermediate acid containing membrane, if present, may be comprised of an organic acid such as fumaric acid, citric acid, succinic acid, tartaric acid, malic acid, and maleic acid; and a binder such as PVP. The nature of the binder is not critical, but water or alcohol soluble polymers are usually used. The weight of this acid coating is about 5 to 20% based on the total weight of the coated beads. The acid in this membrane delays dissolution of the enteric polymer in the inner layer thereby increasing the lag time as well as decreasing the rate of release of the active ingredient from the coated bead. The composition of the outer layer of the polymeric membrane, as well as the individual weights of the inner, intermediate and outer membrane layers are optimized to achieve pulsatile release profiles for a given therapeutic agent or agents, which are predicted based on in vitro/in vivo correlations.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of water insoluble polymers useful in the invention include cellulose derivatives (e.g. ethylcellulose), polyvinyl acetate (Kollicoat SR30D from BASF), neutral copolymers based on ethyl acrylate and methylmethacrylate, copolymers of acrylic and methacrylic acid esters with quaternary ammonium groups, such as Eudragit NE, RS or RS30D, RL or RL30D and the like.

Both enteric and water insoluble polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying the pulsatile release membrane coatings or to separate the different membrane layers by applying a thin hydroxypropyl methylcellulose (HPMC) (Opadry Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention also provides a method of manufacturing a timed pulsatile release dosage form which comprises:

coating an inert particle such as a non-pareil seed (sugar sphere), with a drug and polymeric binder or preparing a drug containing particle by granulation or/and extrusion/spheronization to form an active drug particle;

coating said active drug particle with a plasticized enteric coating which forms a plasticized enteric coated drug particle; and coating said plasticized enteric coated drug particle with a mixture of a water insoluble polymer and an enteric polymer.

The second and third operations can be interchanged and this feature affords an added flexibility in modulating the release profile from said drug particle. Another added flexibility of the present invention is the optional application of an organic acid (such as fumaric or succinic acid) containing membrane between the second and third coating operations to further modulate the lag time and release profile from the drug particle.

Dosage forms incorporating the multicoated drug containing particles in accordance with the invention may take a variety of forms. In one embodiment the formulation may employ a single form of the particulate to provide a time-controlled pulsatile release of the drug several hours after oral administration or to target to specific absorption sites, such as at or near the duodenum/jejunum or colon. In another embodiment, the formulation may contain two or more drug particles with different release characteristics, viz., combination of one or more modified release beads with distinctly different lag times and release rates with or without an immediate release bead to form said timed pulsatile release drug delivery system. The multicoated particulates of two or more drugs can also be combined to obtain synergistic efficacy and patient compliance.

The therapeutic agents suitable for incorporation into these time-controlled or position-controlled pulsatile release systems include acidic, basic, zwitterionic, or neutral organic/inorganic bioactive molecules or their salts. The drug substance can be selected from the group of pharmaceutically acceptable organic or inorganic chemicals with proven pharmacological activity in humans. Representative active compounds include analgesics, anticonvulsants, anesthetics, antidiabetic agents, anti-infective agents, antineoplastics, antiParkinsonian agents, antirheumatic agents, cardiovascular agents, central nervous system (CNS) stimulants, dopamine receptor agonists, gastrointestinal agents, psychotherapeutic agents, or urinary tract agents. Representative examples of specific therapeutic agents or drugs suitable for use in the invention include, but are not limited to, albuterol sulfate, amoxicillin, bupropion hydrochloride, carbidopa, cefaclor, diclofenac sodium, erythromycin, felodipine, loratidine, lithium carbonate, methyl phenidate, metaprolol tartrate, nifedipine, omeprazole, sotalol hydrochloride, verapamil hydrochloride or a therapeutically relevant combination thereof. The above list of drugs is not intended to be exhaustive. Many other drugs are suitable for use in the present invention either singly or in combination with other drugs. The aqueous solubility of the drug can vary from about 0.01 to about 1,000 mg/mL.

The following non-limiting examples illustrate the dosage formulations in accordance with the invention:

EXAMPLE 1

Sotalol HCl (194.7 g) is slowly added to an aqueous solution of polyvinylpyrrolidone (9.8 g Povidone K-30) and mixed well. Sugar spheres (750 g. 20–25 mesh) are coated with the drug solution in a Versa Glatt fluid bed granulator. The drug containing particles are dried and a sealcoat of Opadry Clear (2% w/w) is applied thereto. The first coating is applied to the active particles by spraying on a suspension of Eudragit L30D (480.8 g); acetyl tri-n-butyl citrate (14.4 g); micronized talc (28.8 g) and purified water (462.8 g). The second or outer coating is prepared by mixing two separate aqueous dispersions. The first dispersion is prepared by adding acetyl tri-n-butyl citrate (26.7 g) and Eudragit L30D (891.5 g) to purified water (995.9 g). A second dispersion is prepared by adding dibutyl sebacate (59.5 g) to Aquacoat, a 30 wt. % ethylcellulose dispersion from FMC. The two dispersions are blended together (1:1 ratio) with continuous agitation. The combined coating formulation is then slowly sprayed onto the active particles coated with the first coating. The multicoated particles are cured at 45 to 70° C. until the polymers are coalesced. The final compositions of the multicoated particles of Example 1 are presented in Table 1.

Two lots of finished particles with identical drug contents and inner coating but having the outer coating at 45 and 55% w/w were tested for in vitro dissolution properties in a USP Dissolution Apparatus 2 at 37° C. at a paddle speed of 50 rpm in 0.1N HCl for 2 hours and then at pH 6.8 for an additional 4 hours. The results obtained are presented in Table 2. The dissolution results show that there is a lag time of three to four hours depending on the level of second/outer coating applied and almost complete drug release occurring within 90 min. Similar results have been achieved for methylphenidate hydrochloride using the composition and procedure of Example 1.

TABLE 1

Formulation of Example 1

| Ingredient | 2nd Coating (45% w/w) | 2nd Coating (55% w/w) |
| --- | --- | --- |
| Core | | |
| Sotalol HCl, USP | 8.80 | 7.20 |
| #25 mesh Sugar spheres, NF | 33.91 | 27.72 |
| Povidone, USP | 0.43 | 0.36 |
| Seal Coating | | |
| Opadry Clear YS-1-7006 | 0.88 | 0.72 |
| Inner Coating | | |
| Methacrylic acid copolymer, Type C, NF | 8.46 | 6.92 |
| Talc, USP | 1.69 | 1.39 |
| Acetyl tri-n-butyl citrate | 0.85 | 0.69 |
| Outer Coating | | |
| Methacrylic acid copolymer | 20.47 | 25.04 |
| Acetyl tri-n-butyl citrate | 2.02 | 2.47 |
| Ethylcellulose Aqueous Dispersion, NF | 18.14 | 22.16 |
| Dibutyl Sebacate, NF | 4.36 | 5.33 |
| Purified Water, USP | Trace | Trace |

TABLE 2

Dissolution Data for Example 1

| Time (hours) | 2nd Coating (45% w/w) | 2nd Coating (55% w/w) |
| --- | --- | --- |
| 1 | 0 | 0 |
| 2 | 0 | 0 |
| 3 | 0 | 0 |
| 4 | 81.2 | 0.2 |
| 4.33 | 95.0 | — |
| 5 | — | 70 |
| 5.67 | — | 92.5 |

Although the inventors do not wish to be bound by any theory of operation, the mechanism of release is believed to be as follows: The second coating, which is a matrix coating, is held in place by the ethylcellulose polymer. During the first two hours of dissolution testing in 0.1N hydrochloric acid, drug is not released because the enteric polymer in both the inner and outer membranes is impermeable to 0.1N HCl. When the dissolution medium is changed to pH 6.8, the enteric polymer starts dissolving from the outer membrane, and pores and channels are formed. It takes a while for the dissolution medium to enter the core to dissolve the active and trigger its release, and hence results in additional lag time.

EXAMPLE 2

This Example is based on the use of solutions of the enteric polymer and the ethylcellulose in organic solvents. The sotalol hydrochloride containing particles are produced following the procedure of Example 1. These particles are coated to a 20% weight gain by spraying an enteric polymer (hydroxypropylmethyl cellulose phthalate) solution comprising of 98 parts of acetone and 2 parts of water. The second coating is applied using a solution of ethylcellulose 10 cps and hydroxypropyl methylcellulose phthalate (HPMC phthalate) in equal amounts in a solvent comprising 98 parts of acetone and 2 parts of water. The final compositions of the multicoated particles of Example 2 are presented in Table 3. The finished coated particles are tested for in vitro dissolution as described in Example 1 and the results obtained are presented in Table 4.

TABLE 3

Formulations of Examples 2

| Ingredient | 2nd Coating (35% w/w) | 2nd Coating (40% w/w) |
| --- | --- | --- |
| Core | | |
| Sotalol HCl | 10.40 | 9.60 |
| #25 mesh Sugar spheres | 40.05 | 36.97 |
| Povidone | 0.51 | 0.47 |
| Seal Coating | | |
| Opadry Clear YS-1-7006 | 1.04 | 0.96 |
| Inner Coating | | |
| HPMC phthalate, NF | 10.40 | 9.6 |
| Diethyl phthalate | 2.60 | 2.4 |
| Outer Coating | | |
| HPMC phthalate | 14.00 | 16.00 |
| Ethylcellulose 10 cps, NF | 15.93 | 18.20 |
| Diethyl phthalate | 5.07 | 5.80 |

TABLE 4

Dissolution Data for Example 2

| Time (hours) | 2nd Coating (45% w/w) | 2nd Coating (55% w/w) |
|---|---|---|
| 1 | 0 | 0 |
| 2 | 0 | 0 |
| 3 | 0 | 0 |
| 4 | 2.74 | 1.6 |
| 4.33 | 7.1 | 2.1 |
| 4.67 | 21.5 | 4.1 |
| 5 | 45.3 | 10 |
| 5.33 | 70.5 | 22.9 |
| 5.67 | 89.7 | 42.8 |
| 6.0 | 101.9 | 65.1 |
| 6.33 | | 84.8 |
| 6.67 | | 99.3 |

It is obvious from Table 4 that the use of the solvent applied coating results in lag times similar to those achieved at higher levels of the aqueous coating. For example, a 35 wt. % solvent coating has a lag time similar to that of the 55 wt. % aqueous coating.

EXAMPLE 3

The multicoated beads with the formula of 2$^{nd}$ Coating (at equal amounts for a weight gain of 45% w/w) of Example 1 are produced except that the inner and outer coatings are switched. The dissolution data obtained presented in Table 5 indicate that the invention has the flexibility of interchanging the inner and outer coatings.

TABLE 5

Dissolution Data for Example 3

| Time (hours) | Inner Coating (45% w/w) |
|---|---|
| 1 | 0 |
| 2 | 0 |
| 2.5 | 0 |
| 3 | 71.3 |
| 3.5 | 95.1 |
| 4 | 101.7 |

EXAMPLE 4

The drug layered non-pareil seeds are coated with an Eudragit L30D dispersion for 20% weight gain following the procedure of Example 1. A fumaric acid/PVP composition is applied on these coated beads for a weight gain of 24% w/w. The outer membrane applied is composed of the enteric polymer and ethylcellulose at 1:1 ratio. The final compositions of the multicoated particles of Example 4 are presented in Table 6. The finished coated particles are tested for in vitro dissolution as described in Example 1 and the results obtained are presented in Table 7. It is evident from Tables 2 and 7 that a longer lag time of four hours is achieved at the outer level of 45% w/w. Furthermore, the drug is released not as a pulse but is spread over 6 to 7 hours.

TABLE 6

Formulations of Example 4

| Ingredient | Outer Coating (30% w/w) | Outer Coating (45% w/w) |
|---|---|---|
| Core | | |
| Sotalol HCl | 8.51 | 6.42 |
| Sugar spheres (20–25 mesh) | 32.78 | 26.03 |
| Povidone | 0.42 | 0.33 |
| Seal Coating | | |
| Opadry Clear YS-1-7006 | 0.85 | 0.67 |
| Inner Coating | | |
| Methacrylic acid Copolymer | 8.18 | 6.43 |
| Acetyl tri-n-butyl citrate | 0.82 | 0.64 |
| Talc | 1.64 | 1.29 |
| Intermediate Coating | | |
| Fumaric acid | 15.12 | 11.88 |
| Povidone | 1.68 | 1.32 |
| Outer Coating | | |
| Methacrylic acid Copolymer | 13.65 | 20.46 |
| Acetyl tri-n-butyl citrate | 1.35 | 2.03 |
| Ethylcellulose Dispersion | 12.09 | 18.14 |
| Dibutyl sebacate | 2.91 | 4.36 |

TABLE 7

Dissolution Data for Example 4

| Time (hours) | Outer Coating (30% w/w) | Outer Coating (45% w/w) |
|---|---|---|
| 1 | 0 | 0 |
| 2 | 0.3 | 0 |
| 3 | 9.6 | 0.1 |
| 4 | 27.3 | 7.7 |
| 5 | 56.2 | 18.7 |
| 6 | 77.2 | 37.4 |
| 7 | 89.5 | 54.8 |
| 8 | 97.1 | 67.0 |
| 9 | | 76.4 |
| 10 | | 83.5 |
| 11 | | 89.8 |
| 12 | | 94.3 |

While the invention has been described in detail and with respect to specific embodiments thereof, it will be apparent that numerous modifications and variations are possible without departing from the scope of the invention as defined by the following claims.

What is claimed is:

1. A pharmaceutical dosage form which comprises a plurality of core particles, each core particle containing a drug; said particle being coated with:
   a) a first membrane of an enteric polymer;
   b) a second membrane of a combination of a water-insoluble polymer and an enteric polymer; and
   c) an intermediate membrane comprising an organic acid between the first and second membranes,
wherein said water-insoluble and said enteric polymers are present in said second membrane at a weight ratio of about 10:1 to 1:1,
the total weight of the first and second coatings is about 15 to 80 wt. % based on the total weight of the coated particles; and wherein the first and second membranes can be coated on the core particle in either order.

2. A pharmaceutical dosage form as defined in claim 1 wherein said intermediate membrane further comprises a polymeric binder.

3. A pharmaceutical dosage form as defined in claim 1 wherein the intermediate membrane is about 5% to about 20% of the total weight of the coated particles.

4. A pharmaceutical dosage form as defined in claim 1 wherein the aqueous solubility of said drug varies from about 0.1 mg/mL to about 1,000 mg/mL.

5. A pharmaceutical dosage form as defined in claim 1 wherein the drug substance is selected from the group consisting of analgesics, anticonvulsants, anesthetics, antidiabetic agents, anti-infective agents, antineoplastics, antiParkinsonian agents, antirheumatic agents, cardiovascular agents, central nervous system (CNS) stimulants, dopamine receptor agonists, gastrointestinal agents, psychotherapeutic agents, urinary tract agents or combinations thereof.

6. A pharmaceutical dosage form as defined in claim 1 wherein the drug substance is selected from the group consisting of albuterol sulfate, amoxicillin, bupropion hydrochloride, carbidopa, cefaclor, diclofenac sodium, erythromycin, felodipine, loratidine, lithium carbonate, methylphenidate, metaprolol tartrate, nifedipine, omeprazole, sotalol hydrochloride, verapamil hydrochloride and combinations thereof.

7. A pharmaceutical dosage form as defined in claim 1 wherein the core particle is a non-pareil sugar seed coated with a drug and polymeric binder or the core particle is a particle prepared by granulation and milling or by extrusion/spheronization to form an active drug particle.

8. A pharmaceutical dosage form as defined in claim 1 wherein said enteric polymer is selected from the group consisting of esters of cellulose, polyvinyl acetate phthalate, pH sensitive methacrylic-methylmethacrylate copolymers and shellac.

9. A pharmaceutical dosage form as defined in claim 1 wherein said water insoluble polymer of the second coating is selected from the group consisting of ethylcellulose, polyvinyl acetate, neutral copolymers based on ethyl acrylate and methylmethacrylate and copolymers of acrylic and methacrylic acid esters having quaternary ammonium groups.

10. A pharmaceutical dosage form as defined in claim 1 wherein at least one of said membranes further comprises a plasticizer.

11. A pharmaceutical dosage form as defined in claim 10 wherein said plasticizer is selected from the group consisting of triacetin, tri-butyl citrate, tri-ethyl citrate, acetyl tri-n-butyl citrate, diethyl phthalate, castor oil, dibutyl sebacate, acetylated monoglycerides and mixtures thereof.

12. A pharmaceutical dosage form as defined in claim 1 wherein said membrane coating is applied from a solution in a pharmaceutically acceptable solvent or from an aqueous dispersion of the enteric polymer, water insoluble polymers or their mixtures.

13. A pharmaceutical dosage form as defined in claim 1 wherein said second coating of a mixture of water insoluble and enteric polymers is applied to a thickness of from about 35% to about 55% based on the total weigh of the dosage form.

14. A pharmaceutical dosage form as defined in claim 1 wherein said organic acid of the intermediate membrane applied between the first and second membranes is selected from the group consisting of fumaric acid, succinic acid, tartaric acid, citric acid, malic acid, maleic acid and combinations thereof.

15. A pharmaceutical dosage form as defined in claim 1 wherein said pharmaceutical dosage form is in the form of a hard gelatin capsule.

16. A pharmaceutical dosage form as defined in claim 15 wherein said capsule comprises a single form of the particle to provide a time-controlled pulsatile release of the drug three to six hours upon oral administration.

17. A pharmaceutical dosage form as defined in claim 15 wherein said capsule comprises a single form of the particle to provide a time-controlled pulsatile release of the drug at or near a patient's duodenum/jejunum or colon.

18. A pharmaceutical dosage form as defined in claim 15 wherein said capsule comprises two or more populations of multicoated drug particles wherein each population exhibits different release characteristics.

19. A pharmaceutical dosage form as defined in claim 15 wherein said capsule contains multicoated particles of two or more drugs.

20. A pharmaceutical dosage form of claim 1, wherein the dosage form is prepared by a method comprising the steps of:
   a) preparing a core particle comprising a drug;
   b) coating said drug-containing core particle with a plasticized enteric polymer membrane;
   c) coating said plasticized enteric coated drug particle with an intermediate membrane containing an organic acid; and
   d) coating the intermediate membrane with a membrane comprising a mixture of a water insoluble polymer and enteric polymer wherein said water insoluble polymer and said enteric polymer are present at a weight ratio of from about 10:1 to 1:1;
   wherein the total weight of the coatings is about 15 to 80 weight percent based on the total weight of the coated particles.

* * * * *